United States Patent [19]

Ho et al.

[11] Patent Number: 5,294,578
[45] Date of Patent: Mar. 15, 1994

[54] SUPPORTED ACID CATALYSTS, THEIR PREPARATION AND USE IN ORGANIC COMPOUND CONVERSION

[75] Inventors: Suzzy C. Ho, Plainsboro; Margaret M. Wu, Skillman, both of N.J.

[73] Assignee: Mobil Oil Corp., Fairfax, Va.

[21] Appl. No.: 996,385

[22] Filed: Dec. 23, 1992

[51] Int. Cl.$^5$ .............................................. B01J 29/04
[52] U.S. Cl. ........................................ 502/62; 502/63; 502/64; 502/80; 502/152; 502/154; 502/227; 502/231
[58] Field of Search .............. 502/150, 151, 224, 263, 502/414, 171, 231, 355, 62, 63, 64, 80, 152, 154, 227

[56] References Cited

U.S. PATENT DOCUMENTS

| | | | |
|---|---|---|---|
| 3,248,343 | 4/1966 | Kelly et al. | 252/442 |
| 4,719,190 | 1/1988 | Drago et al. | 502/64 |
| 4,740,652 | 4/1988 | Frame | 585/512 |
| 5,166,410 | 11/1992 | Fried | 554/223 |

OTHER PUBLICATIONS

*Inorganic Chemistry*, vol. 29, No. 6, 1990, pp. 1186–1192.
Krzywicki et al., "Superacidity of Modified Gamma-Al$_2$O$_3$", J. C. S. Faraday I, 1980, 76, 1311–1322.

*Primary Examiner*—Patrick P. Garvin
*Assistant Examiner*—Brent M. Peebles
*Attorney, Agent, or Firm*—Alexander J. McKillop; Dennis P. Santini; Laurence P. Hobbes

[57] ABSTRACT

A novel method to prepare a solid acid catalyst through the reaction of a metal-alkyl halide species and the surface hydroxyl group of a solid support is disclosed. Lewis acidic metals, e.g., B, Al and Ga, etc., can then be anchored on the surface via the formation of an oxygen-metal bond. The solids containing these metals can be used as catalysts that will catalyze organic compound coversion reactions, e.g., Friedel-Crafts type reactions, olefin oligomerization, aromatic alkylation and acylation, alkane alkylation and isomerization reactions.

15 Claims, No Drawings

SUPPORTED ACID CATALYSTS, THEIR PREPARATION AND USE IN ORGANIC COMPOUND CONVERSION

BACKGROUND OF THE INVENTION

1. Field of the Invention

This invention relates to supported acid catalysts, their method of preparation and use in hydrocarbon conversion reactions. The catalyst composition contains metal halides on a solid inorganic oxide support. The composition is prepared by reacting an adsorbent solid support containing surface hydroxide groups with organic metal halide wherein said metal is a single element selected from one of Groups IIA, IIB, IIIA, IIIB, IVB, VB, and VIB, e.g., Al, under conditions sufficient for the organic metal halide to react with at least a portion of the surface hydroxyl groups.

2. Prior Art

Conventional Friedel-Crafts catalysts, e.g., $AlCl_3$ and $BF_3$, have been used extensively in many industrial processes as well as in the laboratory. The major drawback of these systems is the need to dispose of large volumes of liquid and gaseous effluents produced during subsequent quenching and product washing. Replacing these processes by those based on heterogeneous catalysis has environmental and economic advantages, e.g., ease of separation, catalyst recycling and elimination of quenching and washing steps.

The literature discloses efforts to anchor $AlCl_3$ onto a solid support. Alumina can be chlorided with $AlCl_3$, HCl, or $Cl_2$. U.S. Pat. No. 3,248,343 to Kelly et al. teaches the treatment of surface hydroxyl-containing supports, e.g., alumina or silica gel, with aluminum halide and thereafter treating with hydrogen halide. Refluxing $AlCl_3$ with solid supports, e.g., silica, in chlorinated solvent, e.g., $CCl_4$, is an alternate way of anchoring Lewis acid onto a support as disclosed in U.S. Pat. No. 4,719,190 to Drago et al and Getty et al., "Preparation, Characterization, and Catalytic Activity of a New Solid Acid Catalyst System," *Inorganic Chemistry*, Vol. 29, No. 6, 1990 1186–1192. However, these methods suffer from incomplete reaction between $AlCl_3$, HCl or $Cl_2$ and the support, resulting in a catalyst that either contains a low concentration of the acidic species or is not very stable due to the leachability of physisorbed or chemisorbed $AlCl_3$ species from the solid support. Krzywicki et al., "Superacidity of Modified Gamma-$Al_2O_3$, " J.C.S. Faraday I, 1980, 76 1311–1322, teach the treatment of alumina with a metalalkyl species, e.g., $CH_3AlCl_2$ vapors, to prepare a superacid catalyst which can catalyze the transformation of saturated hydrocarbons. U.S. Pat. No. 4,740,652 to Frame discloses an olefin oligomerization catalyst which comprises a porous support, e.g., silica, and plural metal components, an iron group metal, e.g., Ni, and alkyl aluminum compound, e.g., diethylaluminum chloride and aluminum halide, e.g., aluminum trichloride. Such catalysts are used in transition metal catalyzed chemistry.

BRIEF SUMMARY OF THE INVENTION

The present invention relates to a method of preparing a catalyst composition consisting essentially of halides of a single metal component anchored on an adsorbent solid by an oxygen-metal bond. The method comprises contacting an adsorbent inorganic oxide support containing surface hydroxyl groups with organic metal halide, under conditions sufficient for the organic metal halide to react with at least a portion of the surface hydroxyl groups. The metal can be a single element selected from one of Groups IIA, IIB, IIIA, IIIB, IVB, VB, and VIB, and the adsorbent inorganic oxide support is selected from the group consisting of silica, silica-alumina, clay, crystalline porous silicates, silicoaluminophosphates, titania, vanadia, and rare earth oxides. Reaction between the organic metal halide and the surface hydroxyl group can proceed readily at moderate conditions, e.g., room temperature and atmospheric pressure, eliminating the organic ligand and forming a metal-oxygen bond. For example, aluminum alkyl halide reacts with surface hydroxyl groups of a silanol-containing support as follows:

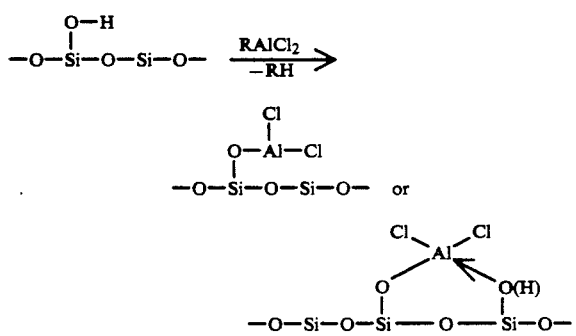

The catalyst compositions thus prepared comprise Lewis acidic catalysts, e.g., $AlCl_3$, $BF_3$, and $GaCl_3$, anchored on the support surface by formation of an oxygen-metal bond. The resulting solid catalysts containing these metals will catalyze hydrocarbon conversion reactions such as Friedel-Crafts type reactions, olefin oligomerization, aromatic alkylation, alkane alkylation and isomerization reactions.

In another aspect, the invention relates to the preparation of a solid acid catalyst composition which consists essentially of halides of at least one major group element (non-transition elements) on an inorganic oxide adsorbent solid support containing surface silanol groups. Such major group metals include Lewis acidic metals such as Al, B, and Ga. Such a composition is prepared by reacting an adsorbent solid support containing surface silanol groups with organic metal halide wherein said metal is one or more major group elements, e.g., Lewis acidic metals (e.g., Al, B, and Ga), under conditions sufficient for the organic metal halide to react with at least a portion of the surface hydroxyl groups.

DETAILED DESCRIPTION OF THE INVENTION

The inorganic porous support materials useful in the present invention are typically inorganic oxides of silica, silica-alumina, silica-thoria, silica-zirconia, clays, crystalline silicates, e.g., zeolites, and silicoaluminophosphates (SAPOs) and comparable oxides which are porous, and have surface hydroxyl groups, viz., silanol groups. Other suitable inorganic porous support materials include titania, zirconia, alumina, vanadia, and rare-earth oxides which have surface hydroxyl groups.

Preferred silica support materials are amorphous silica, silica gels or xerogels with high porosity, preferably having pores of at least 10 Angstroms, more preferably at least 20 Angstroms, e.g., 20 to 460 Angstroms or 60 to 250 Angstroms. Suitable particle sizes for such silica supports range from 1 to 600 mesh, preferably 30 to 400 mesh, e.g., 30 to 60 or 90 to 300 mesh size. The solid support materials can be calcined, preferably under an inert gas, e.g., nitrogen, at a suitable temperature for a sufficient time to remove physically-bound water and/or to partially remove chemically-bound water. Such temperatures can range from about 100° to 900° C., preferably 300° to 600° C., and contacting times can range from 0.1 to 24 hours, preferably 1 to 8 hours. The extent of loading of the halides of a single metal component on the hydroxyl-containing support can be increased by moderating the calcination carried out upon the support prior to contact with the organic metal halide, e.g., reducing calcination temperatures from about 600° C. to 300° C. This is especially effective with silica gel supports. Generally, after treatment with organic metal halide, the metal halides are present in the amount of 0.01 to 10 mmole/g of the catalyst composition.

Naturally occurring clays which can be used as supports herein include the montmorillonite and kaolin families which include the subbentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as rigid three-dimensional frameworks of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed wherein the ratio of aluminum to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic zeolites. The zeolites have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), zeolite ZSM-35 (U.S. Pat. No. 4,016,245), zeolite ZSM-38 (U.S. Pat. No. 4,046,859), zeolite ZSM-23 (U.S. Pat. No. 4,076,842) and MCM-22 (U.S. Pat. No. 4,954,325) merely to name a few.

Silicoaluminophosphates of various structures are taught in U.S. Pat. No. 4,440,871 include SAPO-5, SAPO-11, SAPO-16, SAPO-17, SAPO-20, SAPO-31, SAPO-34, SAPO-35, SAPO-37, SAPO-40, SAPO-41, SAPO-42, and SAPO-44. Other teachings of silicoaluminophosphates and their synthesis include U.S. Pat. No. 4,673,559 (two-phase synthesis method); 4,623,527 (MCM-10); 4,639,358 (MCM-1); 4,647,442 (MCM-2); 4,664,897 (MCM-4); 4,639,357 (MCM-5); 4,632,811 (MCM-3); and 4,880,611 (MCM-9).

Mesoporous siliceous materials are recent developments in catalyst technology having novel pore geometry which are suitable as molecular sieves having openings of at least 8 Angstroms which are used as components of the layered catalyst of the present invention. Such materials can be described as inorganic, porous non-layered crystalline phase material exhibiting, after calcination, an X-ray diffraction pattern with at least one peak at a d-spacing greater than about 18 Angstrom Units and having a benzene adsorption capacity of greater than 15 grams benzene per 100 grams of said calcined material at 50 torr and 25° C. Such materials can further be characterized by substantially uniform hexagonal honeycomb microstructure, with uniform pores having a cell diameter greater than 13 Angstrom units, say, 15 Angstrom Units (preferably in the mesoporous range of about 20–100A). Most prominent among these ultra-large pore size materials is a class of materials known as M41S which are described further in U.S. Pat. No. 5,102,643, including a metallosilicate called MCM-41, which is usually synthesized with Bronsted acid active sites by incorporating a tetrahedrally coordinated trivalent element, such as Al, Ga, B, or Fe, within the silicate framework. Aluminosilicate materials of this type are thermally and chemically stable, properties favored for acid catalysis; however, the advantages of mesoporous structures may be utilized by employing highly siliceous materials or crystalline metallosilicate having one or more tetrahedral species having varying degrees of acidity. In addition to the preferred aluminosilicates, the gallosilicate, ferrosilicate and borosilicate materials may be employed. Although matrices may be formed with the germanium analog of silicon, these are expensive and generally no better than the metallosilicates.

MCM-41 crystalline structure is readily recognized by its spectrographic characteristics, such as electron micrograph, X-ray diffraction pattern, absorption properties, etc., as described in U.S. Pat. No. 5,098,684.

All of the above patents are incorporated herein by reference.

The organic metal halide employed in the present invention can comprise one or more metal elements selected from Groups IIA, IIB, IIIA, IIIB, IVB, VB, and VIB of the Periodic Table, under conditions sufficient for the organic metal halide to react with at least a portion of the surface hydroxyl groups. Suitable organic metal halides include those represented by the formula RMXY wherein R is alkyl, alkenyl, or aryl, M is an element selected from Groups IIA, IIB, IIIA, IIIB, IVB, VB, and VIB of the Periodic Table, X is halogen and Y is selected from the group consisting of halogen, alkyl, alkenyl, aryl, alkoxy, and amido moieties. In one embodiment, R is alkyl, M is a Group IIIA element, e.g., Al, B, or Ga, and Y is selected from the group consisting of halogen, e.g., Cl or Br, and alkyl. A particularly preferred organic metal halide is one wherein RMXY is selected from the group consisting of $EtAlCl_2$, $Me_2AlCl$, $Et_2AlCl$, $Et_2AlCl/EtAlCl_2$, and $Et_2AlOMe$, with $EtAlCl_2$ particularly preferred.

Generally, the support is combined with a suitable solvent in amounts sufficient to form a slurry. The slurry is then combined with the organic metal halide which can also be combined with a suitable solvent in order to facilitate handling and mixing. Such solvents are preferably inert to reaction with the support and organic metal halide. Examples of suitable solvents include alkanes which are liquid under standard conditions such as $C_4$ to $C_{16}$ alkanes, e.g., n-pentane, n-hexane, or n-heptane.

The conditions used to prepare the catalysts of the present invention are those which allow the organic metal halide to react with at least a portion of the surface hydroxyl groups on the adsorbent solid support. Suitable conditions for contacting the support with organic metal halide comprise temperatures of $-78°$ to $120°$ C., pressures of $10^{-6}$ atm to 10 atm, and reaction time of 0.01 to 10 hours. Preferred conditions include temperatures of $20°$ to $60°$ C., pressures of $10^{-1}$ to 1 atm, and reaction time of 0.5 to 2 hours. It is preferred that the catalysts of the present invention be prepared under an inert atmosphere, e.g., nitrogen or helium, in order to prevent unwanted hydrolysis of the organic metal halides. Such conditions can be obtained using conventional Schlenk line techniques.

Following the reaction, the catalyst may be separated from the reaction mixture according to any conventional procedure for removing solids from the liquid solvent medium, e.g., decantation or filtration. The catalyst is ready for use after the drying step as described below. In another method of preparation, the resulting solid can be washed with a suitable liquid, e.g. inert organics, e.g., anhydrous $C_4$ to $C_6$ alkanes, e.g., n-hexane. Such washing is preferably carried out a sufficient number of times to substantially remove excess organic metal halides. The washed catalyst is then dried, preferably under vacuum, at temperatures ranging from $0°$ to $120°$ C., preferably $20°$ to $60°$ C. The dried catalyst is then stored under inert atmosphere, e.g., in a nitrogen filled box.

The amount of metal halides or organo-metal halides deposited onto the solid can range from 0.01 mmole to 10 mmoles of metal halides or organometal halides per g of catalyst. Generally, the lower calcination temperature for the solid, the more organometal halide one can deposit onto the solid.

The catalyst thus prepared is suited to use in the catalytic conversion of organic, e.g., hydrocarbon feeds. In general, catalytic conversion conditions over the present catalyst include a temperature of from about $-100°$ C. to about $760°$ C., a pressure of from about 0.1 atmosphere (bar) to about 200 atmospheres (bar), a weight hourly space velocity of from 0.08 to 2000 $hr^{-1}$ and a hydrogen/organic, e.g., hydrocarbon, compound ratio of from 0 to 100.

Non-limiting examples of such conversion processes include: cracking hydrocarbons with reaction conditions including a temperature of $300°$ to $700°$ C., a pressure of 0.1 to 30 atmospheres (bar) and a weight hourly space velocity of from 0.1 to 20 $hr^{-1}$; dehydrogenating hydrocarbon compounds with reaction conditions including a temperature of $300°$ to $700°$ C., a pressure of 0.1 to 10 atmospheres (bar) and a weight hourly space velocity of from 0.1 to 20 $hr^{-1}$; converting paraffins to aromatics with reaction conditions including a temperature of $100°$ to $700°$ C., a pressure of 0.1 to 60 atmospheres (bar) and a weight hourly space velocity of from 0.5 to 400 $hr^{-1}$ and a hydrogen/hydrocarbon ratio of from 0 to 20; converting olefins to aromatics, e.g., benzene, toluene and xylenes, with reaction conditions including a temperature of $100°$ to $700°$ C., a pressure of 0.1 to 60 atmospheres (bar) and a weight hourly space velocity of from 0.5 to 400 $hr^{-1}$ and a hydrogen/hydrocarbon ratio of from 0 to 20; converting alcohols, e.g., methanol, or ethers, e.g., dimethylether, or mixtures thereof, to hydrocarbons including aromatics with reaction conditions including a temperature of $275°$ to $600°$ C., a pressure of 0.5 to 50 atmospheres (bar) and a weight hourly space velocity of from 0.5 to 100 $hr^{-1}$; isomerizing xylene feedstock components with reaction conditions including a temperature of $230°$ to $510°$ C., a pressure of 3 to 35 atmospheres (bar), a weight hourly space velocity of from 0.1 to 200 $hr^{-1}$, and a hydrogen/hydrocarbon ratio of from 0 to 100; disproportionating toluene with reaction conditions including a temperature of $200°$ to $760°$ C., a pressure of atmospheric to 60 atmospheres (bar) and a weight hourly space velocity of from 0.08 to 20 $hr^{-1}$.

The catalysts of the present invention are particularly useful in processes which rely on a cationic mechanism. e.g., acidic catalysis reactions. All these reactions can be carried out in a fixed-bed, continuous flow reactor or in a slurry, batch-type operation or continuous stirred tank reactor (CSTR) type operation. Such reactions include olefin oligomerization or polymerization reactions with reaction conditions including a temperature of $-100°$ to $300°$ C., preferably $-50°$ to $200°$ C., a pressure of $10^{-6}$ to 60 atmospheres (bar), preferably 0.1 to 10 atmospheres (bar) and a weight hourly space velocity of from 0.1 to 400, preferably 0.1 to 20; Friedel-Crafts alkylation reactions with olefins, alkyl halides or benzyl halides, with reaction conditions including a temperature of $-100°$ to $300°$ C., preferably $-50°$ to $200°$ C., a pressure of 0.1 to 60 atmospheres (bar), preferably 0.1 to 10 atmospheres (bar) and a weight hourly space velocity of from 0 1 to 400, preferably 0.1 to 20; and alkane isomerization reactions with reaction conditions including a temperature of $0°$ to $400°$ C., preferably $100°$ to $300°$ C., a pressure of 0.1 to 60 atmospheres (bar), preferably 0.1 to 20 atmospheres (bar) and a weight hourly space velocity of from 0.1 to 400, preferably 0.1 to 20.

In order to more fully illustrate the nature of the invention and the manner of practicing same, the following examples are presented. It will be understood that the examples are illustrative only and that various modifications may be made in the specified parameters without departing from the scope of the invention.

EXAMPLE 1

In a 100 mL Schlenk flask was placed 10 g of 20A silica gel (calcined at $600°$ C. under nitrogen for 15 hours and stored under nitrogen atmosphere) and 40 mL of anhydrous hexane. 5 g of 25 wt % solution of EtAlCl$_2$ in hexane was added to the slurry via syringe. During the addition-step a stoichiometric amount of ethane evolution was observed. The mixture was stirred at room temperature for one hour. The supernatant was removed and the solids were washed with 20 mL of anhydrous hexane three times. The solids were dried under vacuum at room temperature or 50° C. for one hour.

EXAMPLES 2-12

The method in Example 1 was used with different silica and reagents as indicated in Table 1.

pared from the 40A silica is less active achieving only 15% hexene conversion in one hour compared to 99% conversions of similar catalysts prepared from 60A and 150A silica;

b) As expected, the catalyst with two chlorine ligands on the aluminum is more active than those containing at least one alkyl or alkoxy ligand. Since alkyl and alkoxy groups are electron donating, the aluminum center with those ligands are less Lewis acidic than those with two chlorine ligands;

c) Catalysts prepared from supports (Examples 3 and 9) calcined at two difference temperatures do not show

TABLE 1

| | | Catalyst Preparation | | |
|---|---|---|---|---|
| EXAMPLE | SUPPORT | CALCINATION TEMP* | REAGENT | Al:SUPPORT (mmol:g) |
| 1 | 20A silica | 600° C. | EtAlCl$_2$ | <<1.0:1** |
| 2 | 40A silica | 600° C. | EtAlCl$_2$ | 1.0:1 |
| 3 | 60A silica | 600° C. | EtAlCl$_2$ | 1.0:1 |
| 4 | 150A silica | 600° C. | EtAlCl$_2$ | 1.0:1 |
| 5 | 60A silica | 300° C. | EtAlCl$_2$ | 1.0:1 |
| 6 | 60A silica | 300° C. | EtAlCl$_2$ | 2.0:1 |
| 7 | 60A silica | 600° C. | EtAlCl$_2$ | 2.0:1 |
| 8 | 60A silica | 600° C. | Me$_2$AlCl | 1.0:1 |
| 9 | 60A silica | 600° C. | Et$_2$AlCl | 1.0:1 |
| 10 | 60A silica | 600° C. | Et$_2$AlCl/ EtAlCl$_2$ | 1.0:1 |
| 11 | 60A silica | 600° C. | Et$_2$AlOMe | 1.0:1 |
| 12 | 50A MCM-41 | 538° C. | EtAlCl$_2$ | 1.0:1 |
| 8 | gamma Al$_2$O$_3$ | 600° C. | EtAlCl$_2$ | 1.0:1 |

*By titration, SiO2 calcined at 300° C. contains 3.0 mmol of Si—OH/g of SiO$_2$
By titration, SiO2 calcined at 600° C. contains 2.1 mmol of Si—OH/g of SiO2
**Reaction between Si—OH and EtAlCl2 was minimal as indicated by the removal of EtAlCl$_2$ during subsequent hexane wash.

EXAMPLES 14-24

The activities of the catalysts shown in Table 1 were tested for aromatic alkylation with toluene and 1-hexane and the results are shown in Table 2.

significant difference in the toluene-hexene alkylation reaction; and d) Catalysts with different aluminum loading cannot be differentiated by the toluene-hexene reaction at room temperature.

TABLE 2

Toluene Alkylation with 1-Hexene
(20 mL of Toluene and 10 mL of 1-Hexene
over 0.5 g of Catalyst at Room Temperature)

| EXAMPLE | CATALYST | REACTION TIME, h | % 1-HEXENE CONVERSION | PRODUCT DISTRIBUTION (ALKYLATED) | | |
|---|---|---|---|---|---|---|
| | | | | MONO- | DI- | TRI- |
| 14 | Ex. 1 | 20 | 0.1 | — | — | — |
| 15 | Ex. 2 | 1 | 14.8 | 59.1 | 21.4 | 19.5 |
| 16 | Ex. 3 | 1 | 99.0 | 64.2 | 24.2 | 11.6 |
| 17 | Ex. 4 | 1 | 99.0 | 64.9 | 27.1 | 8.0 |
| 18 | Ex. 5 | 1 | 94.5 | 71.8 | 22.1 | 6.1 |
| 19 | Ex. 6 | 1 | 98.8 | 73.1 | 22.5 | 4.4 |
| 20 | Ex. 7 | 1 | 98.4 | 59.3 | 25.2 | 15.5 |
| 21 | Ex. 8 | 48 | 97.1 | 63.1 | 22.8 | 9.2 |
| 22 | Ex. 9 | 90 | 18.9 | 75.9 | 15.0 | 7.5 |
| 23 | Ex. 10 | 99 | 98.1 | 59.3 | 23.5 | 17.2 |
| 24 | Ex. 11 | 49 | 0.2 | 67.9 | 22.8 | 9.2 | a) The activities depend on pore size of the silica. Extremely low hexene conversion was observed for catalyst prepared from the 20A silica. This is the result of lower amount of Al deposited (see Table 1) on the SiO$_2$ as well as the small pore size. The catalyst pre-

EXAMPLES 25-34

The catalyst prepared according to Example 3 was used for various Friedel-Crafts aromatic alkylation reactions shown in Table 3.

TABLE 3

| | Friedel-Crafts Aromatic Alkylation | | | | |
|---|---|---|---|---|---|
| Ex. | AROMATIC COMPOUND (1) | ALKYLATING AGENT (2) | REACTANT RATIO (mole) 1:2:CATALYST | ALKYLATING CONDITION | CONVERSION AGENT |
| 25 | Benzene | 1-Decene | 222:111:1 | <34° C., 2 h | 99% |

TABLE 3-continued

| | | Friedel-Crafts Aromatic Alkylation | | | |
|---|---|---|---|---|---|
| Ex. | AROMATIC COMPOUND (1) | ALKYLATING AGENT (2) | REACTANT RATIO (mole) 1:2:CATALYST | ALKYLATING CONDITION | CONVERSION AGENT |
| 26 | Diphenylether | 1-Dodecene | 222:111:1 | 100° C., 3.5 h | 80% |
| 27 | Naphthalene | 1-Dodecene | 222:111:2 | 48° C., 19 h | 98% |
| 28 | Phenol | 1-Dodecene | 111:55:1 | 100° C., 19 h | 1.5% |
| 29 | Benzene | 2-Chlorobutane | 555:28:1 | 50° C., 1 h | 99% |
| 30 | Benzene | Dibromomethane | 555:28:1 | 50° C., 2.5 h | 45% |
| 31 | Benzene | Dichlorotoluene | 555:28:1 | 50° C., 17 h | 21% |
| 32 | Chlorobenzene | Dichlorotoluene | 555:28:1 | 50° C., 1 h | 41% |
| 33 | Benzene | Benzyl chloride | 555:55:1 | 50° C., 2.5 h | 56% |
| 34 | Fluorobenzene | Benzyl chloride | 555:55:1 | 50° C., 19 h | 50% |

It is claimed:

1. A method of preparing a catalyst composition consisting essentially of halides of a single metal component anchored on an adsorbent solid by an oxygen-metal bond which comprises contacting an adsorbent inorganic oxide support containing surface hydroxyl groups with organic metal halide, under conditions sufficient for said organic metal halide to react with at least a portion of said surface hydroxyl groups wherein said metal is aluminum, and said adsorbent inorganic oxide support is selected from the group consisting of silica, silica-alumina, clay, crystalline porous silicates, silicoaluminophosphates, titania, vanadia, and rare earth oxides.

2. The method of claim 1 wherein said surface hydroxyl groups are silanol, said organic metal halide has the formula RMXY wherein R is alkyl or aryl, M is aluminum, X is halogen and Y is selected from the group consisting of halogen, alkyl, alkenyl, aryl, alkoxy, and amido moieties.

3. The method of claim 1 wherein said inorganic oxide support is calcined at temperatures ranging from 100° to 900° C. prior to said contacting.

4. The method of claim 1 wherein said inorganic oxide support is calcined at temperatures ranging from 300° C. to 600° C. for 1 to 8 hours, prior to said contacting.

5. The method of claim 1 wherein said halides of a single metal component are present in the amount of 0.01 to 10 mmole/g of said catalyst composition.

6. The method of claim 1 wherein said inorganic oxide support is silica.

7. The method of claim 1 wherein said inorganic oxide support is a porous crystalline silicate selected from the group consisting of MCM-22 and MCM-41.

8. The method of claim 2 wherein R is alkyl and Y is selected from the group consisting of halogen and alkyl.

9. The method of claim 8 wherein X is Cl.

10. The method of claim 2 wherein RMXY is selected from the group consisting of etAlCl$_2$, Me$_2$AlCl, Et$_2$AlCl, Et$_2$AlCl/EtAlCl$_2$, and Et$_2$AlOMe.

11. The method of claim 2 wherein RMXY is EtAlCl$_2$ and said adsorbent is silica.

12. The method of claim 1 wherein said conditions comprise temperatures of $-78°$ to 120° C., pressures of $10^{-6}$ to 10 atm, and reaction time of 0.01 to 10 hours.

13. The method of claim 1 wherein said conditions comprise temperatures of 20° to 60° C., pressures of 0.1 to 1 atm, and reaction time of 0.5 to 2 hours.

14. The catalyst composition prepared according to the method of claim 1.

15. The catalyst composition prepared according to the method of claim 2.

* * * * *